US008831737B2

(12) United States Patent
Wesselink

(10) Patent No.: US 8,831,737 B2
(45) Date of Patent: *Sep. 9, 2014

(54) ACTIVITY SENSING FOR STIMULATOR CONTROL

(71) Applicant: Medtronic, Inc., Minneapolis, MN (US)

(72) Inventor: Wilbert A. Wesselink, Doesburg (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,163

(22) Filed: May 31, 2013

(65) Prior Publication Data
US 2013/0268022 A1     Oct. 10, 2013

Related U.S. Application Data

(63) Continuation of application No. 13/403,288, filed on Feb. 23, 2012, now Pat. No. 8,483,839, which is a continuation of application No. 12/181,013, filed on Jul. 28, 2008, now Pat. No. 8,155,753, which is a continuation of application No. 11/116,969, filed on Apr. 28, 2005, now Pat. No. 7,406,351.

(51) Int. Cl.
| A61B 5/103 | (2006.01) |
| A61B 5/117 | (2006.01) |
| A61B 8/12 | (2006.01) |
| A61B 5/107 | (2006.01) |
| A61B 5/11 | (2006.01) |
| A61N 1/05 | (2006.01) |

(52) U.S. Cl.
CPC .............. *A61B 5/107* (2013.01); *A61B 5/1118* (2013.01); *A61N 1/0531* (2013.01); *A61N 1/0534* (2013.01)
USPC ................... 607/62; 607/117; 607/2; 607/46

(58) Field of Classification Search
USPC ............................................... 607/2, 62, 117
See application file for complete search history.

(56) References Cited

U.S. PATENT DOCUMENTS

| 4,977,895 A | 12/1990 | Tannenbaum |
| 5,031,618 A | 7/1991 | Mullett |

(Continued)

FOREIGN PATENT DOCUMENTS

| EP | 0410734 B1 | 1/1991 |
| EP | 0547482 A1 | 6/1993 |

(Continued)

OTHER PUBLICATIONS

Dijkstra, "Ultrasonic distance detection for spinal cord stimulation," Ph.D. Thesis, Chapter 6, pp. 116-117 (2003).

(Continued)

*Primary Examiner* — Carl H Layno
*Assistant Examiner* — John Eric C Morales
(74) *Attorney, Agent, or Firm* — Shumaker & Sieffert, P.A.

(57) ABSTRACT

The disclosure describes a system that measures the distance between one or more electrodes and tissue of a patient, and controls one or more parameters of the stimulation delivered to the tissue by the electrodes based on the measured distance. The system controls the measurement of the distance between the electrodes and the tissue as a function of activity of the patient. The system uses, for example, a piezoelectric transducer to sense activity of the patient, and may determine whether or how frequently to measure the distance between electrodes and tissue based on the sensed physical activity. A piezoelectric transducer may be used both to sense activity and to measure the distance between the electrodes and the tissue.

32 Claims, 7 Drawing Sheets

(56) References Cited

U.S. PATENT DOCUMENTS

| | | | |
|---|---|---|---|
| 5,111,813 A | 5/1992 | Charbonnier et al. | |
| 5,246,463 A | 9/1993 | Giampapa | |
| 5,342,404 A * | 8/1994 | Alt et al. | 607/6 |
| 5,593,431 A | 1/1997 | Sheldon | |
| 5,628,317 A | 5/1997 | Starkebaum et al. | |
| 5,716,377 A | 2/1998 | Rise et al. | |
| 5,775,331 A | 7/1998 | Raymond et al. | |
| 5,814,092 A | 9/1998 | King | |
| 5,836,983 A | 11/1998 | Weijand et al. | |
| 5,941,906 A | 8/1999 | Barreras, Sr. et al. | |
| 6,029,090 A | 2/2000 | Herbst | |
| 6,032,674 A | 3/2000 | Eggers et al. | |
| 6,319,241 B1 | 11/2001 | King et al. | |
| 6,339,724 B1 | 1/2002 | Thong | |
| 6,393,325 B1 | 5/2002 | Mann et al. | |
| 6,466,817 B1 | 10/2002 | Kaula et al. | |
| 6,500,128 B2 | 12/2002 | Marino | |
| 6,564,078 B1 | 5/2003 | Marino et al. | |
| 6,684,106 B2 | 1/2004 | Herbst | |
| 6,752,765 B1 | 6/2004 | Jensen et al. | |
| 6,795,737 B2 | 9/2004 | Gielen et al. | |
| 6,978,178 B2 | 12/2005 | Sommer et al. | |
| 6,993,384 B2 | 1/2006 | Bradley et al. | |
| 7,031,773 B1 | 4/2006 | Levine et al. | |
| 7,139,608 B2 | 11/2006 | Ideker et al. | |
| 7,389,147 B2 | 6/2008 | Wahlstrand et al. | |
| 7,406,351 B2 * | 7/2008 | Wesselink | 607/62 |
| 7,647,121 B2 | 1/2010 | Wahlstrand et al. | |
| 7,720,548 B2 | 5/2010 | King | |
| 7,974,698 B2 | 7/2011 | Tass et al. | |
| 8,108,049 B2 | 1/2012 | King | |
| 8,121,702 B2 | 2/2012 | King | |
| 8,150,530 B2 | 4/2012 | Wesselink | |
| 8,155,753 B2 * | 4/2012 | Wesselink | 607/62 |
| 8,457,759 B2 | 6/2013 | Parker et al. | |
| 8,483,839 B2 | 7/2013 | Wesselink | |
| 2001/0053885 A1 * | 12/2001 | Gielen et al. | 604/20 |
| 2002/0107553 A1 | 8/2002 | Hill et al. | |
| 2002/0123773 A1 | 9/2002 | Molin | |
| 2002/0133206 A1 | 9/2002 | Daum et al. | |
| 2003/0040776 A1 | 2/2003 | Kroll et al. | |
| 2003/0105503 A1 | 6/2003 | Marino | |
| 2003/0120323 A1 | 6/2003 | Meadows et al. | |
| 2003/0153959 A1 | 8/2003 | Thacker et al. | |
| 2003/0176807 A1 | 9/2003 | Goetz et al. | |
| 2003/0181960 A1 | 9/2003 | Carter et al. | |
| 2003/0199929 A1 | 10/2003 | Snyder et al. | |
| 2003/0199938 A1 | 10/2003 | Smits et al. | |
| 2004/0015205 A1 | 1/2004 | Whitehurst et al. | |
| 2004/0024421 A1 | 2/2004 | Ideker et al. | |
| 2004/0044377 A1 | 3/2004 | Larsson | |
| 2004/0078058 A1 | 4/2004 | Holmstrom et al. | |
| 2004/0102712 A1 | 5/2004 | Belalcazar et al. | |
| 2004/0111124 A1 | 6/2004 | Walker et al. | |
| 2004/0111130 A1 | 6/2004 | Hrdlicka et al. | |
| 2004/0116784 A1 | 6/2004 | Gavish et al. | |
| 2004/0116978 A1 | 6/2004 | Bradley | |
| 2004/0122486 A1 | 6/2004 | Stahmann et al. | |
| 2004/0138516 A1 | 7/2004 | Osorio et al. | |
| 2004/0147983 A1 | 7/2004 | Czygan | |
| 2004/0158119 A1 | 8/2004 | Osorio et al. | |
| 2004/0220637 A1 | 11/2004 | Zdeblick et al. | |
| 2004/0243192 A1 | 12/2004 | Hepp et al. | |
| 2004/0254483 A1 | 12/2004 | Zdeblick et al. | |
| 2005/0049646 A1 | 3/2005 | Czygan et al. | |
| 2005/0081847 A1 | 4/2005 | Lee et al. | |
| 2005/0119703 A1 | 6/2005 | DiLorenzo | |
| 2005/0216062 A1 | 9/2005 | Herbst | |
| 2005/0222626 A1 | 10/2005 | DiLorenzo | |
| 2005/0240242 A1 | 10/2005 | DiLorenzo | |
| 2006/0004424 A1 | 1/2006 | Loeb et al. | |
| 2006/0009816 A1 | 1/2006 | Fang et al. | |
| 2006/0036186 A1 | 2/2006 | Goetz et al. | |
| 2006/0247732 A1 | 11/2006 | Wesselink | |
| 2006/0259079 A1 | 11/2006 | King | |
| 2007/0055315 A1 | 3/2007 | Ideker et al. | |
| 2007/0156206 A1 | 7/2007 | Wahlstrand et al. | |
| 2008/0281379 A1 | 11/2008 | Wesselink | |
| 2008/0288031 A1 | 11/2008 | Wesselink | |
| 2012/0109254 A1 | 5/2012 | King | |

FOREIGN PATENT DOCUMENTS

| | | |
|---|---|---|
| EP | 0904739 A2 | 3/1999 |
| WO | WO 2004/075982 A1 | 9/2004 |
| WO | WO 2004/078252 A2 | 9/2004 |
| WO | WO 2005/065536 A1 | 7/2005 |
| WO | WO 2005/102449 A1 | 11/2005 |

OTHER PUBLICATIONS

Holsheimer et al., "Effect of Anode-Cathode Configuration on Paresthesia Coverage in Spinal Cord Stimulation," WA, Neurosurgery, vol. 41, No. 3, pp. 654-660 (Sep. 1997).

International Search Report and Written Opinion of international application No. PCT/US2006/015388, dated Sep. 25, 2006, 10 pp.

International Preliminary Report on Patentability dated Apr. 12, 2007 for international application No. PCT/US2006/015388, dated Apr. 12, 2007, 8 pp.

Prosecution history from U.S. Appl. No. 11/116,969, dated Apr. 9, 2007 through Mar. 26, 2008, 52 pp.

Prosecution history from U.S. Appl. No. 12/181,013, dated Aug. 23, 2010 through Dec. 13, 2011, 75 pp.

Prosecution history from U.S. Appl. No. 12/181,047, dated Aug. 20, 2010, through Dec. 13, 2011, 81 pp.

Prosecution history from U.S. Appl. No. 13/403,288, dated Oct. 16, 2012, through Mar. 5, 2013, 27 pp.

Prosecution history from U.S. Appl. No. 11/414,534, dated Dec. 17, 2008, through Oct. 3, 2011, 167 pp.

Prosecution history from U.S. Appl. No. 11/414,530, dated Apr. 29, 2009, through May 18, 2010, 41 pp.

Prosecution history from U.S. Appl. No. 12/717,484, dated Oct. 5, 2010, through Oct. 11, 2011, 56 pp.

Prosecution history from U.S. Appl. No. 13/348,943, dated Mar. 19, 2013, through Jul. 19, 2013, 21 pp.

Prosecution history from U.S. Appl. No. 11/119,420, dated Feb. 14, 2007, through Apr. 22, 2008, 77 pp.

Prosecution history from U.S. Appl. No. 11/687,480, dated Mar. 5, 2009, through Nov. 20, 2009, 33 pp.

* cited by examiner

ACTIVITY SENSING FOR STIMULATOR CONTROL

RELATED APPLICATION

This application is a continuation of U.S. application Ser. No. 13/403,288, filed Feb. 23, 2012 (now U.S. Pat. No. 8,483, 839), which is a continuation of U.S. application Ser. No. 12/181,013, filed Jul. 28, 2008 (now U.S. Pat. No. 8,155,753), which is a continuation of U.S. application Ser. No 11/116, 969, filed Apr. 28, 2005 (now U.S. Pat. No. 7,406,351), the entire contents of which are incorporated herein by reference.

TECHNICAL FIELD

The invention relates to medical devices and, more particularly, to medical devices that deliver stimulation.

BACKGROUND

Chronic pain, such as pain in the back, legs or pelvis, is a common symptom that many people endure on a daily basis, and it can significantly lower their quality of life. Chronic pain can be attributed to a variety of ailments that are difficult to treat directly. Some ailments that cause chronic pain include failed back surgery syndrome, reflex sympathetic dystrophy, multiple sclerosis and peripheral arterial disease, and chronic pain may also be caused by poor posture, obesity, trauma or old age. Since medical intervention to correct the cause of chronic pain may not be possible or effective, treatment is often aimed towards suppressing the symptoms, or pain, to increase the quality of life of a patient.

Many different types of treatment may be used to treat chronic pain. Some of these treatments include medication, acupuncture, trigger point injections, physical therapy, exercise, nutritional modifications, and medical devices. Not all treatments are effective for all patients, and a combination of treatments may be prescribed by a physician.

In some cases, chronic pain may be treated with neurostimulation. An implantable medical device may be implanted into the patient at a location near the back or abdomen and used to generate electrical pulses. These pulses may be delivered to the spinal cord through an insulated lead. One or more electrodes at the distal end of the lead conduct the pulses into the surrounding tissue. The lead, or a plurality of leads, may be placed near a certain location on the spine or other area to suppress the pain. Stimulation may help to reduce or relieve the pain by modulating nerve impulses to the brain that signal pain.

SUMMARY

The invention is directed to a system that controls measurement of the distance between one or more electrodes and tissue of the patient to which the electrodes deliver stimulation based on the sensed physical activity. The system may determine whether or how frequently to measure the distance based on the sensed activity. In embodiments in which an implantable medical device (IMD) measures the distance between electrodes and tissue, using an activity measurement to determine when such measurements should occur may preserve battery life of the IMD.

The system includes sensors to sense patient activity and measure the distance between the electrodes and the tissue. For example, the system may include a piezoelectric transducer or accelerometer to sense physical activity, e.g., gross motor movement and/or footfalls, of a patient. The system may also include a piezoelectric transducer to ultrasonically measure the distance between the electrodes and the tissue. In some embodiments, the sensors may be located proximate to the electrodes to detect motion and measure the distance at the site of stimulation, e.g., the sensors may be carried by a lead that includes the electrodes. In some embodiments a piezoelectric transducer both senses activity and measures the distance.

In some stimulation systems, the electrodes that deliver stimulation are not attached to the tissue to which they deliver the stimulation. For example, it is generally undesirable to physically attach electrodes to the spinal cord for delivery of spinal cord stimulation (SCS) therapy. In such systems, patient activity and movement may change the distance between the tissue and the electrodes, e.g., the spinal cord and the electrodes at the distal end of a lead. As the distance changes, the intensity of the stimulation as perceived by the patient may change, which may lead to changes in the efficacy of the stimulation or side effects associated with the stimulation. Consequently, a system according to the invention adjusts stimulation parameter values based on a measured distance between the electrodes and the tissue to compensate for changed distance.

Detecting distance frequently and at a constant rate, e.g., measurements approximately once a minute, may significantly decrease the life of a battery in an IMD, and would result in the distance being measured at times when it is less likely to be changing, i.e., when the patient is recumbent or asleep. Therefore, a system according to the present invention controls distance measurement based on sensed patient activity, e.g., determines whether or how frequently to measure the distance based on the sensed activity. In this way, the system may limit distance measurements when patient activity is nominal, thereby prolonging battery life, while allowing for an increased frequency of measurements during increased physical activity to provide more frequent therapy adjustment to compensate for distance changes.

In one embodiment, the invention is directed to a method comprising sensing activity of a patient, measuring a distance between an electrode and tissue to which the electrode delivers stimulation based on the sensed activity, and adjusting a parameter of the stimulation as a function of the measured distance.

In another embodiment, the invention is directed to a system comprising a first sensor to sense activity of a patient, a second sensor to measure a distance between an electrode and tissue to which the electrode delivers stimulation, and a processor to control the second sensor to measure the distance based on the sensed activity, and adjust a parameter of the stimulation as a function of the measured distance.

In an additional embodiment, the invention provides a system comprising means for sensing activity of a patient, means for measuring a distance between an electrode and tissue to which the electrode delivers stimulation based on the sensed activity, and means for adjusting a parameter of the stimulation as a function of the measured distance.

Although the invention may be especially applicable to spinal cord stimulation systems, the invention alternatively may be applied to other sites of stimulation where the electrodes cannot be physically attached to the tissue of interest. These therapies may include deep brain stimulation, cortical brain stimulation, sacral or pedundal nerve stimulation, or other nervous, cardiac, gastric, muscular, or other tissue stimulation that may relieve conditions other than pain.

In various embodiments, the invention may provide one or more advantages. For example, monitoring patient activity may allow distance detection to occur as needed. During periods in which the patient is recumbent or otherwise stationary, distance detection may not be needed, and battery consumption due to frequent distance measurement can be avoided. The system may detect periods of increasing patient activity. During these periods, the system may measure the distance more frequently. While this may consume more power, the increased measurement frequency may improve the uniformity of the stimulation received at the tissue during such high activity periods by enabling more frequent adjustment of the stimulation parameters.

In some cases, the system may not measure the distance until the activity surpasses a certain threshold. Further, some embodiments may utilize a distance measurement frequency that is a function of the activity level. This relationship may be, for example, linear, step-wise or logarithmic. In addition, the patient or clinician may modify stored measurement/activity or distance/stimulation parameter functions with an external programmer that communicates with the implantable stimulator wirelessly.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
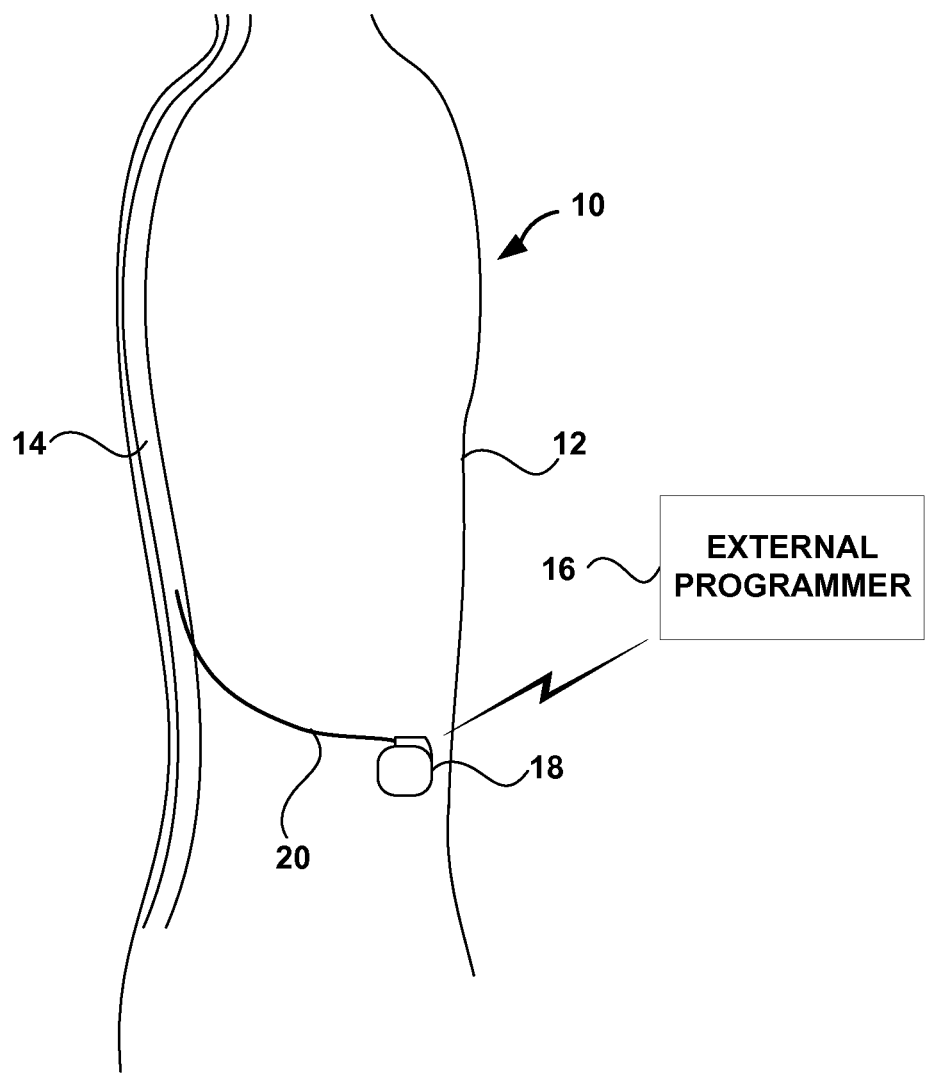
FIG. 1 is a conceptual diagram illustrating an example stimulation system in conjunction with a patient.

FIG. 1 is a conceptual diagram illustrating an example system 10 in conjunction with a patient 12. As shown in FIG. 1, system 10 may include an implantable medical device (IMD) 18 that delivers stimulation to patient 12, and an external programmer 16. IMD 18 is coupled to a lead 20 and delivers stimulation to patient 12 via the lead. More particularly, IMD 18 delivers stimulation via one or more electrodes (not shown in FIG. 1) carried by lead, e.g., located on a distal portion of lead. Although illustrated as coupled to a single lead 20, IMD 18 may be coupled to any number of leads 20.

In the illustrated example, IMD 18 is an implantable neurostimulator that delivers stimulation to the spinal cord 14 of patient 12 via lead 20, i.e., provides spinal cord stimulation (SCS) therapy. However, the invention is not limited to IMDs that deliver SCS therapy, IMDs that deliver neurostimulation therapy, or even to IMDs. The invention may be embodied in systems that include any type of implantable or external medical device that delivers stimulation to tissue of a patient. The one or more electrodes for delivery of stimulation may be, for example, carried by leads, integrated into a housing of a medical device, and/or applied to an external surface, e.g., the skin, of a patient.

As will be described in greater detail below, system 10 measures the distance between the one or more electrodes and the tissue to which the electrodes deliver stimulation from IMD 18, and the adjusts one or more parameters of the stimulation based on the measured distance. In some embodiments, IMD 18 delivers stimulation in the form of electrical pulses. In such embodiments, the stimulation parameters that may be adjusted include voltage or current pulse amplitude, width and rate. In general, the stimulation is adjusted to maintain a substantially consistent level of stimulation current at the tissue despite changes in the distance between the electrodes and the tissue.

System 10 also senses the activity of patient 12, and measures the electrode/tissue distance based on the sensed activity is sensed. In general, the electrode/tissue distance is more likely to vary when the patient is active. Consequently, system 10 may determine whether and/or how often to measures the distance based on the sensed activity in order to provide more frequent measurements and parameter adjustments when necessary, while conserving a power source when frequent measurements and parameter adjustments are not necessary.

In the illustrated example, system 10 includes a external programmer 16 that communicates with IMD 18 via wireless telemetry. A clinician or patient 12 may use programmer 16 to adjust stimulation parameters, or to interrogate IMD 18 for information stored therein, as is known in the art. External programmer 16 may be, for example, a desktop, laptop, tablet, handheld, or other computing device.

In some embodiments, external programmer 16 may be a small, battery-powered, portable device that accompanies the patient 12 throughout a daily routine. In such embodiments, programmer 16 may have a simple user interface, such as a button or keypad, and a display or lights. Patient 12 may initiate, modify or cease stimulation via the user interface.

Although described herein primarily in the context of embodiments in which IMD 18 senses patient activity, measures electrode/tissue distance when activity is sensed, and adjusts one or more parameter values based on the measured distance, the invention is not so limited. For example, in some embodiments, an external computing device, such programmer 16, may perform one or more of these functions. For example, programmer 16 may receive signals indicating patient activity and electrode/tissue distance from IMD via telemetry, and may control the frequency of electrode/tissue distance measurement and adjust stimulation parameters based on the received signals.

Figure 2:
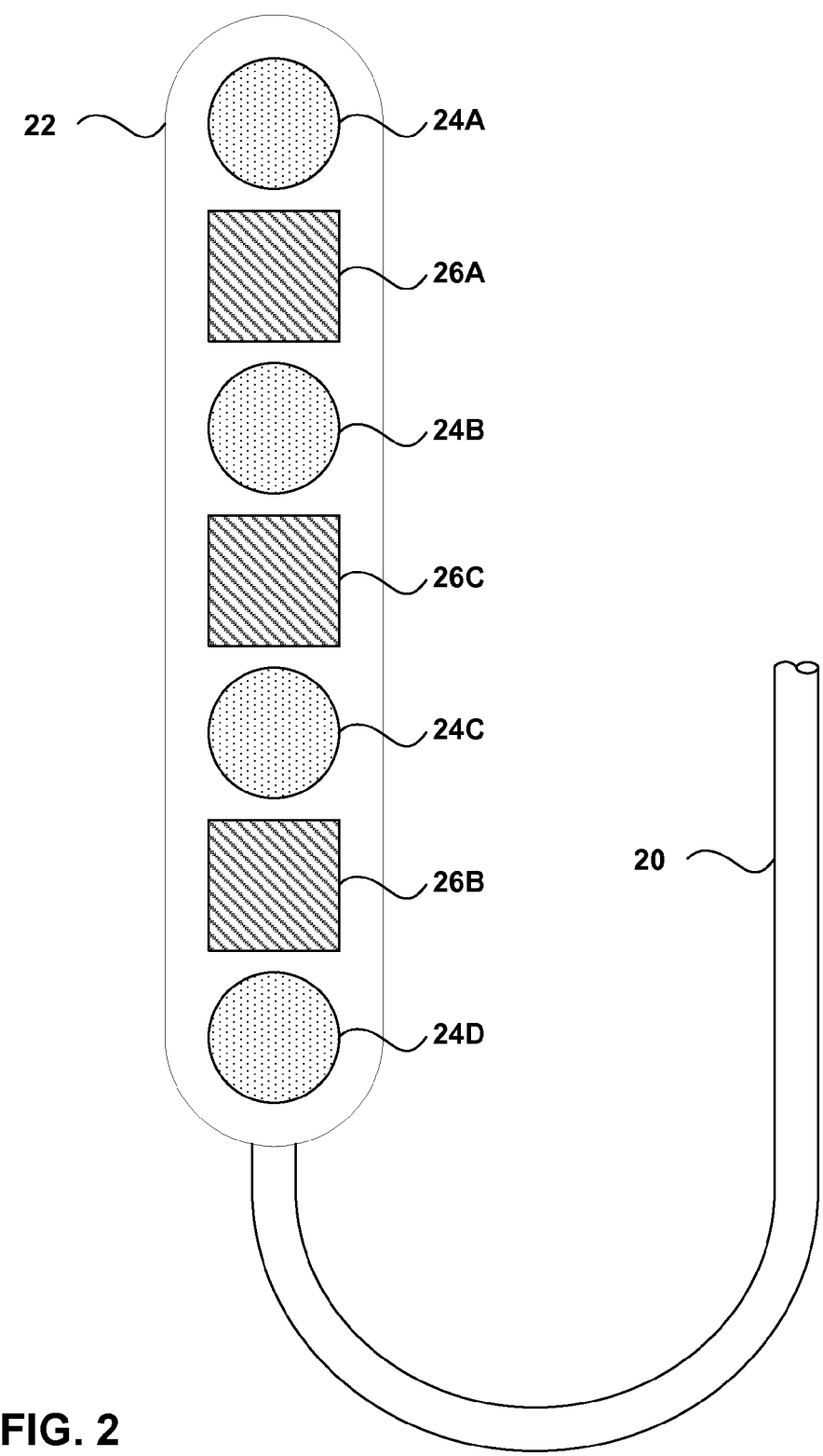
FIG. 2 is a schematic diagram illustrating a distal portion of an implantable lead with several electrodes and piezoelectric transducers.

FIG. 2 is a schematic diagram illustrating a distal portion 22 of lead 20 according to one example embodiment of the invention. In the illustrated example, distal portion 22 includes a plurality of electrodes 24A, 24B, 24C and 24D (collectively, "electrodes 24") and a plurality of piezoelectric transducers 26A, 26B and 26C (collectively, "piezoelectric transducers 26"). Although distal portion 22 is shown as having a "paddle" shape known in the art, the invention is not limited to any particular type of lead. Lead 20 may be any type of percutaneously or surgically implantable lead. Further, the numbers, shapes and locations of electrodes 24 and transducers 26 are merely exemplary In this exemplary embodiment, piezoelectric transducers 26 may be used for two different purposes. Transducers may be used to measure the distance between themselves and the tissue to be stimulated, i.e. spinal cord 14. Each piezoelectric transducer 26 may be composed of two layers that respectively act as an ultrasonic transmitter and an ultrasonic receiver. One layer produces an ultrasonic wave that travels to the tissue where it is partially reflected. The reflected echo wave is received by the other layer of the transducer, at which time the distance can be calculated based on the time between the sent and received waves. This measured distance allows adjustment of pulse parameters in order to provide substantially consistent stimulation intensity regardless of changes in the distance between the distal portion 22, e.g., electrodes 24, and the tissue.

Piezoelectric transducers 26 may also be used to sense physical activity of patient 12. Piezoelectric transducers 26 may transducer vibrations associated with gross motor movement and/or footfalls of patient 12. System 10 may use the magnitude and/or frequency of the vibrations detected by piezoelectric transducers to identify an activity level of patient 12 that may be used to determine whether and/or how frequently to measure the distance between electrodes 24 and the tissue. Piezoelectric transducers 26 may continuously or periodically sense the activity level of patient 12.

In general, the size of the electrodes and piezoelectric transducers would be limited. The diameter of each electrode 26 may be less than 7 mm with a thickness of less than 3 mm. Preferably, the diameter of each electrode would be less than 5 mm with a thickness less than 2 mm. The size of each transducer 26 may be less than 7 mm by 7 mm with a thickness less than 3 mm. Preferably, the transducer would be less than 5 mm by 5 mm with a thickness less than 2 mm. The sizes of each electrode and transducer may not need to be identical as electrodes and transducers of varying sizes may be used on the same distal portion.

In some embodiments, a plurality of piezoelectric transducers 26 sense patient activity, while, in other embodiments, only one of transducers 26 detects activity. Multiple transducers 26 may be placed on different axes in order to more accurately detect motion in a plurality of directions. In some embodiments, transducers 26 are dedicated to either distance measurement or activity sensing, while some embodiments may only include one piezoelectric transducer 26 that both measures distance and senses activity in order to reduce the size of distal end 22.

The invention is not limited to embodiments in which either or both of the activity sensors and distance measurement sensors of system 10 are piezoelectric transducers. In some embodiments, for example, an activity sensor may be an accelerometer, mercury switch, EMG electrode, ECG electrode, or the like, which generate signals that vary as a function of patient activity. Further, the distance measurement sensors may be any type of ultrasonic or non-ultrasonic distance measurement sensor. For example, in some embodiments, distance may be measured optically.

Further, the invention is not limited to embodiments in which such sensors are carried on the same lead as each other or electrodes 24. In general, it is desirable to place distance measurement sensors proximate to electrodes. However, activity sensors may located anywhere within or outside of patient 12.

Figure 3:
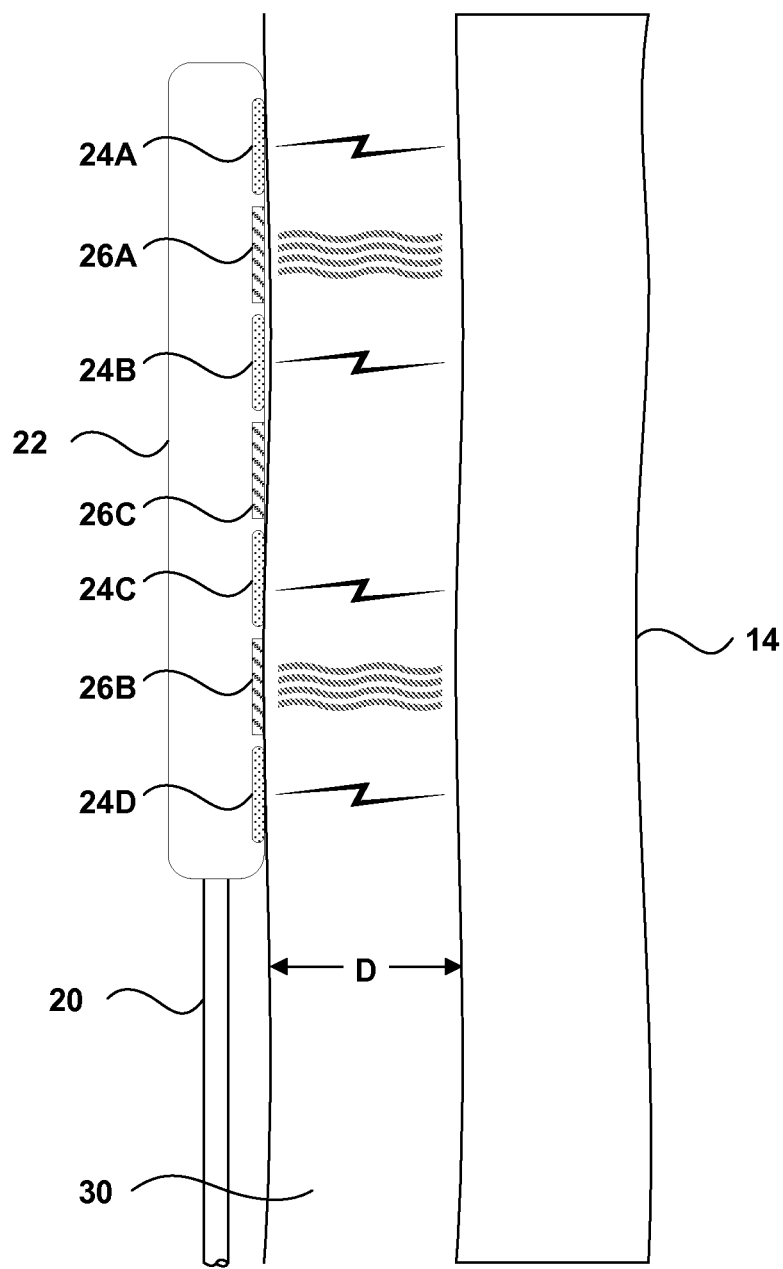
FIG. 3 is a cross-sectional side view of the distal portion of the implantable lead in relation to tissue.

FIG. 3 is a cross-sectional side view of the distal portion 22 of lead 20 in relation to tissue at an intended stimulation site, e.g., spinal cord 14. Electrodes 24 and piezoelectric transducers 26 are aimed through intervening space 30, which may be fluid, towards spinal cord 14. The thickness of space 30 is distance D. The "bolts" illustrated by FIG. 3 signify stimulation from electrodes 24, and the "wavy" lines indicate ultrasonic waves emitted from the piezoelectric transducers 26.

It is desirable to assure that the stimulation from IMD 18 travels through space 30 and still provides appropriate stimulation for effective therapy. For this to occur, the magnitude of space 30, D, is measured periodically as the patient is active. In the illustrated embodiments, piezoelectric transducers 26 are located near the electrodes in case distance D varies along distal portion 22. IMD 18 may be capable of providing stimulation with a different magnitude to each of electrode 24 based on the distance measured proximate to the particular electrode. For example, piezoelectric transducer 26A may measure a larger distance D to the spinal cord than piezoelectric transducer 26B. Therefore, stimulation with greater magnitude may be delivered to electrodes 24A and 24B than electrodes 24C and 24D.

In this embodiment, the center piezoelectric transducer 26C is used to detect activity of patient 12, e.g., motion of distal portion 22. Being located in the center of the distal portion may be beneficial for acquiring an accurate estimate of the motion experienced by the entire distal portion. When activity is detected at the site, piezoelectric transducers 26A and 26B may measure the distance D at their respective locations. Ultrasonic waves are produced in the direction of the tissue which subsequently reflects back as echo waves. The receiving layer of the same transducer detects the echo waves and the distance D is calculated. This distance could be averaged between the two transducers if the distal portion is generally parallel to spinal cord 14. Adjustments to stimulation parameters, e.g., the magnitude of the stimulation delivered by the electrodes 24, are then calculated based upon distance D. In some cases, transducer 26A may be used to measure the distance D for electrodes 26A and 26B while transducer 26B may be used to measure the distance D for electrodes 24C and 24D, as discussed above.

Figure 4:
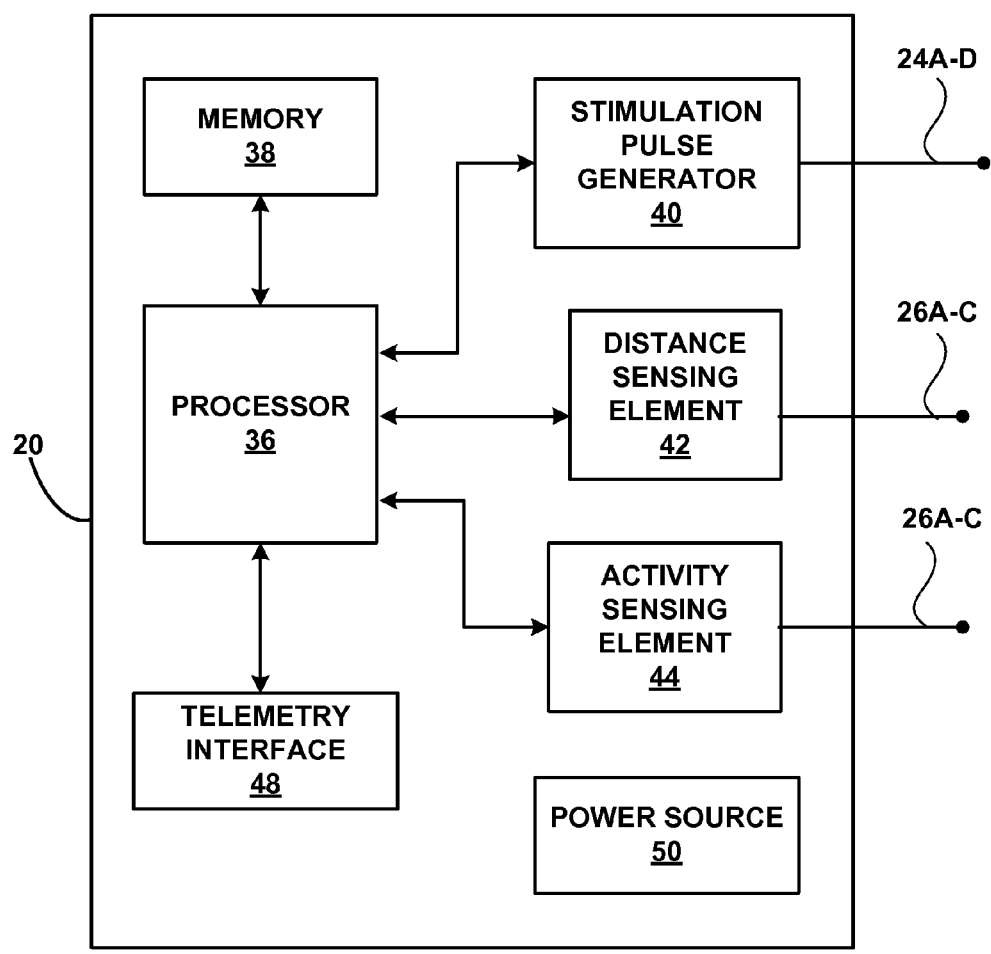
FIG. 4 is functional block diagram illustrating components of an exemplary implantable medical device.

FIG. 4 is a functional block diagram illustrating various components of IMD 18. In the example of FIG. 4, IMD 18 includes a processor 36, memory 38, stimulation pulse generator 40, distance measurement element 42, activity sensing element 44, telemetry interface 48, and power source 50. As shown in FIG. 4, stimulation generator 40 is coupled to electrodes 24, while distance measurement element 42 and activity sensing element 44 are coupled to piezoelectric transducers 26. Alternatively, distance measurement element 42 and activity sensing element 44 may be coupled to any of a variety separate or common distance and activity sensors, as described above.

Processor 36 controls stimulation pulse generator 40 to deliver electrical stimulation therapy according to stimulation parameter values stored in memory 38. Processor 36 may receive such parameter values from programmer 16 via telemetry interface 48. Based on activity information received from the activity sensing element 44, processor determines if and how often distance detection should occur. When appropriate, processor 36 controls distance measurement element 42 to acquire a distance measurement. Processor 36 then determines whether any therapy parameter adjustments should be made based on the measured distance. For example, processor 36 may compare the new distance measurement to the current distance measurement, and make changes to stimulation parameters if they are different. Processor 36 may store the adjustments in memory 38 and provide the adjustments to stimulation generator 20.

As an example, in the presence of patient activity, processor 36 may control distance measurement element 42 to perform a distance measurement. In the case of a distance measurement smaller than the current value, processor 36 may decrease a stimulation parameter, such as pulse amplitude. If the distance measurement is greater than the current value, processor 36 may increase the stimulation parameter. These adjustments would be carried out in order to provide a substantially consistent stimulation intensity at spinal cord 14 regardless of the distance between the electrodes and the spinal cord. Although processor 36 is described in this example as adjusting stimulation parameters, it is noted that the adjustments may be generated by external programmer 16, and more particularly a processor within external programmer 16, as discussed above.

Activity sensing element 44 may comprise amplifiers, filters and other signal processing circuitry to process the signals received from one or more piezoelectric transducers 26. Based on the amplitude and/or frequency of the processed signal, processor 36 may identify an activity level that may be used to determine whether or how often to measure distance.

Distance measurement element 42 may include circuits to drive piezoelectric transducers 26 to output ultrasonic waves in response to a signal from processor 36, and signal processing circuitry to detect and process the returned echo signal. Processor 36 may calculate the electrode/tissue distance based on a signal received from the distance measurement element 42 indicating detection of the echo.

Processor 36 may comprise any one or more of a microprocessor, digital signal processor (DSP), application specific integrated circuit (ASIC), field-programmable gate array (FPGA), or other digital logic circuitry. Memory 38 stores instructions for execution by processor 36, stimulation therapy data, e.g., values for stimulation therapy parameters, activity data and distance data. The activity and distance data are received from distance measurement and activity sensing elements 42 and 44, and may be recorded for long-term storage and retrieval by a user via programmer 16 (FIG. 1) and telemetry interface 48. Memory 38 may include any one or more of a random access memory (RAM), read-only memory (ROM), electronically-erasable programmable ROM (EEPROM), flash memory, or the like.

Wireless telemetry in IMD 18 may be accomplished by radio frequency (RF) communication or proximal inductive interaction of IMD 18 with external programmer 16. This wireless communication is possible through the use of telemetry interface 48. Accordingly, telemetry interface 48 may be similar to the telemetry interface contained within external programmer 16.

Power source 50 delivers operating power to the components of implantable IMD 18. Power source 50 may include a battery and a power generation circuit to produce the operating power. In some embodiments, the battery may be rechargeable to allow extended operation. Recharging may be accomplished through proximal inductive interaction between an external charger and an inductive charging coil within IMD 18. In other embodiments, traditional batteries may be used. As a further alternative, an external inductive power supply could transcutaneously power IMD 18 whenever stimulation is needed or desired.

Measuring the distance between the electrodes and the tissue of interest consumes a small amount of current, but constant detection could significantly shorten the life of an implanted battery designed to last many years. If distance detection occurs at approximately once per minute, the overall lifetime of such a battery may be reduced by approximately 20 percent. Sensing activity may help to limit this decrease in battery life by reducing or eliminating unnecessary distance measuring while the patient is stationary. For example, it would be unnecessary for the distance detection to occur during sleep. This time may take up anywhere from 20 to 40 percent of a patient's day. Alternatively, sensing activity may allow for more distance measurements during periods of a patient's day when the distance may be changing more often. The result is a stimulator system that provides distance measurement when required without sacrificing large losses in battery life.

Figure 5:
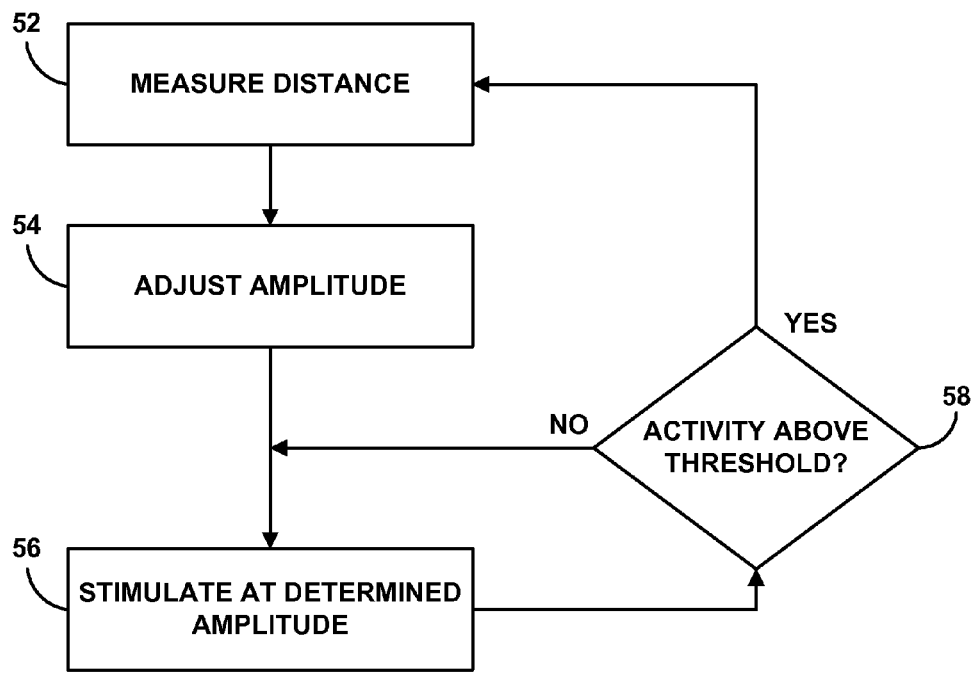
FIG. 5 is a flow diagram illustrating an example technique for detecting the distance between electrodes and tissue based on sensed patient activity during stimulation.

FIG. 5 is a flow diagram illustrating an example technique for detecting the distance between electrodes and tissue based on sensed patient activity during stimulation that may be performed by system 10. In the example of FIG. 5, system 10 measures the distance between the electrodes and tissue to which the electrodes deliver stimulation (52). System 10 uses the distance measurement to determine an adjustment to one or more stimulation parameters, such as pulse amplitude (54). System 10 delivers stimulation at the adjusted parameter values, e.g., with the adjusted amplitude, via the electrodes (56). After stimulation has been delivered, system 10 senses patient activity, and determines whether such activity exceeds a threshold value (58). If no activity is present above a specified threshold, then stimulation continues with current parameters. If activity has been detected above a predetermined threshold, the loop begins again and resets stimulation parameters by measuring the distance and adjusting the parameters based on the measured distance.

Figure 6:
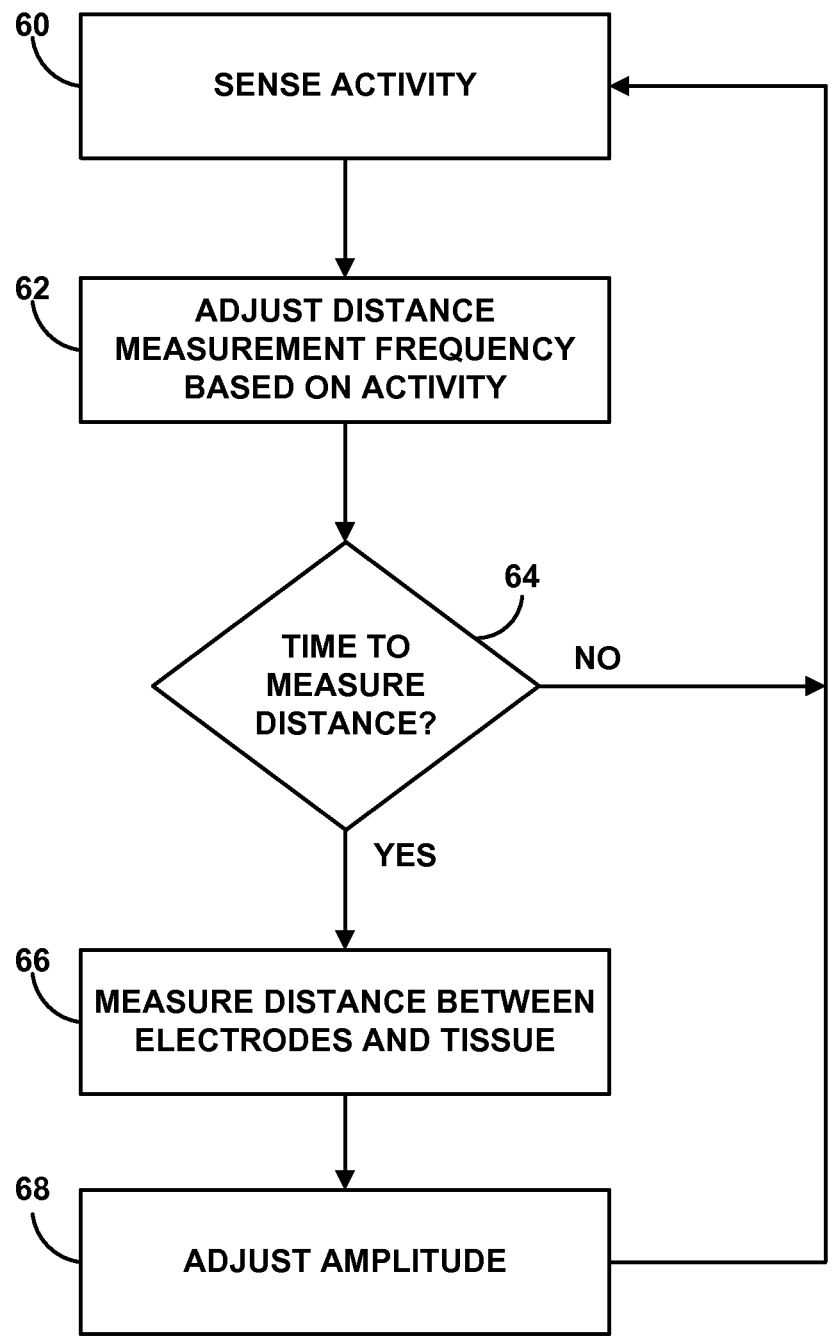
FIG. 6 is a flow diagram illustrating another example technique for detecting the distance between electrodes and tissue based on sensed patient activity during stimulation.
Figure 7A:
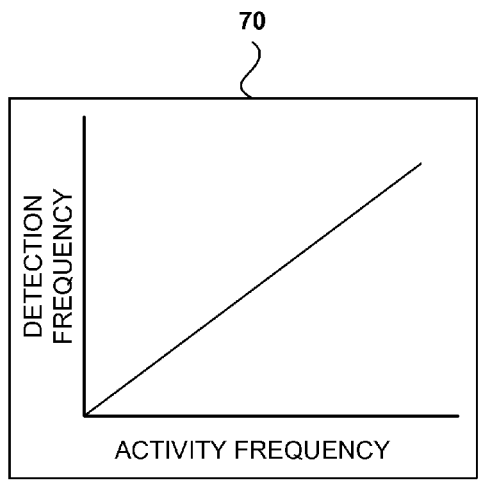
FIGS. 7A-7D are graphs showing exemplary functional relationships between patient activity and frequency of electrode/tissue distance measurements.
Figure 7B:
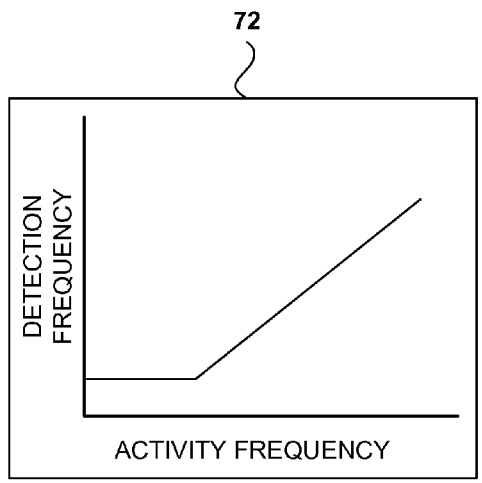
Figure 7C:
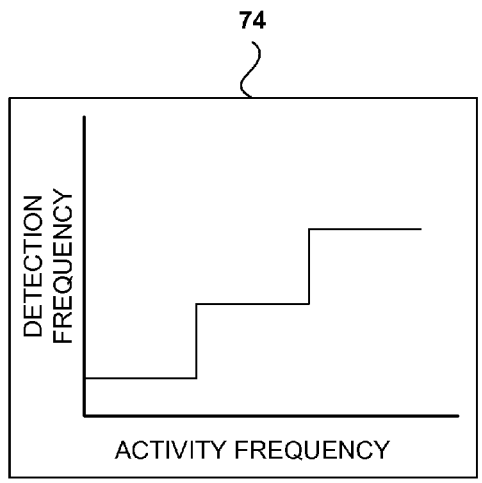
Figure 7D:
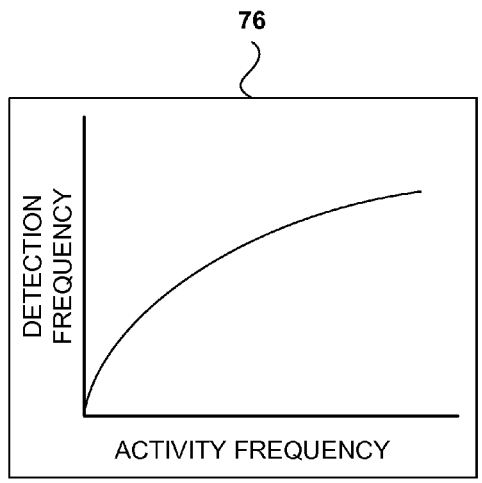

FIG. 6 is a flow diagram illustrating another example technique for detecting the distance between electrodes and tissue based on sensed patient activity during stimulation that may be performed by system 10. In the example of FIG. 6, system 10 determines a patient activity level based on the output of a sensor, such as piezoelectric transducer 26, and adjusts a distance measurement frequency based on the sensed activity level (60, 62). System 10 determines whether it is time for a electrode/tissue distance measurement based on the current frequency (64). If it is not time for a measurement, system 10 continues to monitor the activity level and adjust the measurement frequency. When it is time for a distance measurement, system 10 measures the electrode/tissue distance, and adjusts a stimulation parameter, such as pulse amplitude, based on the measured distance (66, 68)

FIGS. 7A-7D are graphs 70, 72, 74 and 76 showing exemplary functional relationships between the sensed activity and the electrode/tissue measurement frequency. Graph 70 illustrates a linear relationship between activity and the measurement frequency. As the patient moves more frequently, for example, the distance detection may occur more frequently as well in order to provide substantially consistent stimulation at the intended tissue. The slope of the linear function may vary, and a clinician may set the slope to a variety of values.

Graph 72 displays a linear relationship similar to graph 70, however a threshold is also applied. In this embodiment of the function, the measurement frequency always occurs at a nominal frequency when any activity is present. When the activity increases beyond a predetermined threshold, a linear relationship between the sensed activity and measurement frequency is established. The threshold may be set to a variety of values to best treat the patient. In some embodiments, this threshold may indicate that no distance detection should occur under nominal activity until more frequent or strenuous activity is sensed.

The function displayed in graph 74 is a step-wise function to control the detection frequency. In general, there would be three separate levels of distance measurement frequency based upon the activity of the patient. As the activity increases, the frequency of distance measurement increases as well. Some embodiments may include a different number of levels, while the levels in other embodiments may not be uniform in step increases.

In a further embodiment, the functional relationship in graph 76 shows a logarithmic function. When the activity level is low, it may be beneficial to have a larger change in measurement frequency with only a small change in activity level. However, with increasing activity, the measurement frequency necessary for adequate therapy may reach a limit. In this case, very high activity would not require large changes in distance measurement frequency that may only cause increasing drain upon battery resources while not contributing to more effective stimulation.

It should be noted at that all of the functional relationships described in FIG. 7 are only examples, and system 10 may be capable of programming any type of function desired by the clinician. In particular, any of the functions herein may be combined to provide customized activity-based stimulation adjustments for a specific patient. These custom functions may include a variety of thresholds, magnitudes, and curves described by a mathematical equation or sets of mathematical equations.

Although the invention may be especially applicable to the simulation of the spinal cord, the invention alternatively may be applied more generally to any type of stimulation wherein the electrode may move with respect to the targeted tissue. As examples, cortical brain stimulation, deep brain stimulation, sacral or pedundal nerve stimulation, or dorsal root stimulation may benefit from activity regulated distance measurement as described herein. In addition, even electrodes fixed to nervous or muscle tissue may utilize this invention to periodically measure a change in distance with high activity levels or long time periods.

Various embodiments of the described invention may include processors that are realized by microprocessors, Application-Specific Integrated Circuits (ASIC), Field-Programmable Gate Arrays (FPGA), or other equivalent integrated logic circuitry. The processor may also utilize several different types of storage methods to hold computer-readable instructions for the device operation and data storage. These memory and storage media types may include a type of hard disk, random access memory (RAM), or flash memory, e.g. CompactFlash or SmartMedia. Each storage option may be chosen depending on the embodiment of the invention. While the implantable IMD 18 may contain permanent memory, external programmer 16 may contain a more portable removable memory type to enable easy data transfer for offline data analysis.

The preceding specific embodiments are illustrative of the practice of the invention. It is to be understood, therefore, that other expedients known to those skilled in the art or disclosed herein may be employed without departing from the invention or the scope of the claims.

Many embodiments of the invention have been described. Various modifications may be made without departing from the scope of the claims. These and other embodiments are within the scope of the following claims.

The invention claimed is:

1. A system comprising:
  a sensor configured to measure a distance between an electrode and a tissue of a patient to which the electrode delivers stimulation; and
  at least one processor configured to:
    control the sensor to measure the distance between the electrode and the tissue of the patient;
    determine whether the measured distance has changed; and
    responsive to determining that the measured distance has changed, adjust, as a function of the measured distance, a parameter of the stimulation to provide a substantially consistent stimulation intensity at the tissue, wherein adjusting the parameter of the stimulation comprises adjusting a parameter of one or more electrical pulses that are generated by a stimulation generator and that are delivered by the electrode to the tissue of the patient.

2. The system of claim 1,
  wherein the sensor comprises a first sensor,
  wherein the system further comprises a second sensor configured to sense activity of the patient, and
  wherein the at least one processor is configured to determine how frequently to control the first sensor to measure the distance between the electrode and the tissue of the patient as a function of the sensed activity.

3. The system of claim 2, further comprising a lead that carries the electrode and the first and second sensors.

4. The system of claim 2, wherein the second sensor comprises a piezoelectric transducer.

5. The system of claim 2, wherein the first sensor ultrasonically measures the distance.

6. The system of claim 5, wherein the first sensor comprises a piezoelectric transducer.

7. The system of claim 2, wherein the first and second sensors comprise a common piezoelectric transducer.

8. The system of claim 1,
  wherein the sensor comprises a first sensor,
  wherein the system further comprises a second sensor configured to sense activity of the patient, and
  wherein the at least one processor is configured to compare the sensed activity to a threshold value, and to control the first sensor to measure the distance when the sensed activity exceeds the threshold value.

9. The system of claim 1,
  wherein the sensor comprises a first sensor,
  wherein the system further comprises a second sensor configured to sense activity of the patient, and
  wherein the at least one processor is configured to compare the sensed activity to a plurality of thresholds, each of the thresholds associated with a respective one of a plurality of distance measurement frequencies, and to control the first sensor to measure the distance at one of the plurality of frequencies based on the comparison.

10. The system of claim 1, further comprising an implantable medical device that includes the stimulation generator, wherein the implantable medical device is configured to deliver the stimulation via the electrode, and wherein the at least one processor comprises one or more processors of the implantable medical device.

11. The system of claim 1, wherein the tissue comprises tissue of the spinal cord.

12. The system of claim 1, wherein the tissue comprises brain tissue, cardiac tissue, gastric tissue, muscular tissue, or nerve tissue.

13. The system of claim 1, wherein the electrode is implanted within the patient.

14. The system of claim 1, wherein the at least one processor is configured to control the sensor to measure the distance upon receiving an indication of activity of the patient.

15. The system of claim 1, wherein adjusting the parameter of the one or more electrical pulses that are generated by the stimulation generator comprises adjusting at least one of a pulse amplitude, a pulse width, and a pulse rate of the one or more electrical pulses.

16. A system comprising:
  a sensor configured to measure a distance between an electrode and a tissue of a patient to which the electrode delivers stimulation; and at least one processor configured to:
control the sensor to measure the distance upon determining a likelihood that the distance between the electrode and the tissue has changed;
determine whether the measured distance has changed; and
responsive to determining that the measured distance has changed, adjust, as a function of the measured distance, a parameter of the stimulation delivered by the electrode, wherein adjusting the parameter of the stimulation comprises adjusting a parameter of one or more electrical pulses that are generated by a stimulation generator and that are delivered by the electrode to the tissue of the patient.

17. The system of claim 16,
wherein the sensor comprises a first sensor,
wherein the system further comprises a second sensor configured to sense activity of the patient, and
wherein the at least one processor is further configured to determine how frequently to control the first sensor to measure the distance between the electrode and the tissue of the patient as a function of the sensed activity.

18. The system of claim 17, further comprising a lead that carries the electrode and the first and second sensors.

19. The system of claim 17, wherein the second sensor comprises a piezoelectric transducer.

20. The system of claim 17, wherein the first sensor ultrasonically measures the distance.

21. The system of claim 20, wherein the first sensor comprises a piezoelectric transducer.

22. The system of claim 17, wherein the first and second sensors comprise a common piezoelectric transducer.

23. The system of claim 16,
wherein the sensor comprises a first sensor,
wherein the system further comprises a second sensor configured to sense activity of the patient, and
wherein the at least one processor is configured to compare the sensed activity to a threshold value, and to control the first sensor to measure the distance when the sensed activity exceeds the threshold value.

24. The system of claim 16,
wherein the sensor comprises a first sensor,
wherein the system further comprises a second sensor configured to sense activity of the patient, and
wherein the at least one processor is configured to compare the sensed activity to a plurality of thresholds, each of the thresholds associated with a respective one of a plurality of distance measurement frequencies, and to control the first sensor to measure the distance at one of the plurality of frequencies based on the comparison.

25. The system of claim 16, further comprising an implantable medical device that includes the stimulation generator, wherein the implantable medical device is configured to deliver the stimulation via the electrode, wherein the at least one processor comprises one or more processors of the implantable medical device.

26. The system of claim 16, wherein the tissue comprises tissue of the spinal cord.

27. The system of claim 16, wherein the tissue comprises brain tissue, cardiac tissue, gastric tissue, muscular tissue, or nerve tissue.

28. The system of claim 16, wherein the electrode is implanted within the patient.

29. The system of claim 16, wherein the at least one processor is configured to control the sensor to measure the distance upon receiving an indication of activity of the patient.

30. The system of claim 16, wherein adjusting the parameter of the one or more electrical pulses that are generated by the stimulation generator comprises adjusting at least one of a pulse amplitude, a pulse width, and a pulse rate of the one or more electrical pulses.

31. A method comprising:
controlling, by at least one processor, measurement of a distance between an electrode and a tissue of a patient to which the electrode delivers stimulation;
determining, by the at least one processor, whether the measured distance between the electrode and the tissue of the patient has changed; and
responsive to determining that the measured distance has changed, adjusting, by the at least one processor and as a function of the measured distance, a parameter of the stimulation to provide a substantially consistent stimulation intensity at the tissue, wherein adjusting the parameter of the stimulation comprises adjusting a parameter of one or more electrical pulses that are generated by a stimulation generator and that are delivered by the electrode to the tissue of the patient.

32. A method comprising:
controlling, by at least one processor, measurement of a distance between an electrode and a tissue of a patient to which the electrode delivers stimulation upon determining a likelihood that the distance has changed;
determining, by the at least one processor, whether the measured distance between the electrode and the tissue of the patient has changed; and
responsive to determining that the measured distance has changed, adjusting, by the at least one processor and as a function of the measured distance, a parameter of the stimulation delivered by the electrode, wherein adjusting the parameter of the stimulation comprises adjusting a parameter of one or more electrical pulses that are generated by a stimulation generator and that are delivered by the electrode to the tissue of the patient.

* * * * *